United States Patent
Bender et al.

(10) Patent No.: US 7,691,827 B2
(45) Date of Patent: Apr. 6, 2010

(54) AMIDE PRODRUG OF GEMCITABINE, COMPOSITIONS AND USE THEREOF

(75) Inventors: David Michael Bender, Indianapolis, IN (US); David Michael Remick, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 409 days.

(21) Appl. No.: 11/719,705

(22) PCT Filed: Nov. 30, 2005

(86) PCT No.: PCT/US2005/043125

§ 371 (c)(1), (2), (4) Date: May 18, 2007

(87) PCT Pub. No.: WO2006/065525

PCT Pub. Date: Jun. 22, 2006

(65) Prior Publication Data

US 2009/0156547 A1   Jun. 18, 2009

Related U.S. Application Data

(60) Provisional application No. 60/637,422, filed on Dec. 17, 2004.

(51) Int. Cl.
  *A61K 31/70* (2006.01)
  *C07H 19/073* (2006.01)
(52) U.S. Cl. ..................... 514/49; 536/28.51
(58) Field of Classification Search .............. None
  See application file for complete search history.

(56) References Cited

U.S. PATENT DOCUMENTS

| | | | | |
|---|---|---|---|---|
| 4,526,988 A | * | 7/1985 | Hertel | 549/313 |
| 4,692,434 A | * | 9/1987 | Hertel | 514/49 |
| 4,965,374 A | * | 10/1990 | Chou et al. | 549/313 |
| 5,430,026 A | * | 7/1995 | Hertel et al. | 514/43 |
| 5,965,119 A | * | 10/1999 | Greenwald et al. | 424/78.37 |
| 6,303,569 B1 | * | 10/2001 | Greenwald et al. | 514/2 |
| 6,376,470 B1 | * | 4/2002 | Greenwald et al. | 514/43 |
| 6,384,019 B1 | * | 5/2002 | Myhren et al. | 514/49 |
| 6,624,142 B2 | * | 9/2003 | Greenwald | 514/2 |
| 7,265,096 B2 | * | 9/2007 | Gallop et al. | 514/49 |
| 2005/0159375 A1 | * | 7/2005 | Srivastava et al. | 514/44 |

FOREIGN PATENT DOCUMENTS

WO    WO 98/32762 A    7/1998
WO    WO 2004/041203 A    5/2004

OTHER PUBLICATIONS

Immordino, M; Preparation, characterization, cytotoxicity and pharmacokinetics of liposomes containing lipophilic gemcitabine prodrugs; Journal of Controlled Release_2004_vol. 100_pp. 331-346.

* cited by examiner

*Primary Examiner*—Lawrence E Crane
(74) *Attorney, Agent, or Firm*—Elizabeth A. McGraw; Arleen Palmberg

(57) ABSTRACT

The present invention relates to the gemcitabine prodrug 1-(2, 2-difluoro-2-deoxy-β-D -ribofuranosyl)-4-(2-propyl-1-oxo-pentyl)aminopyrimidin-2-one useful as an oral drug for the treatment of cancer.

6 Claims, No Drawings

AMIDE PRODRUG OF GEMCITABINE, COMPOSITIONS AND USE THEREOF

This is a 371 of PCT/US2005/043125 filed 30 Nov. 2005, which claims priority to U.S. Provisional Application No. 60/637,422 filed Dec. 17, 2004.

BACKGROUND OF THE INVENTION

The present invention relates to a novel prodrug of gemcitabine, which is capable of being given orally, traversing the intestinal tract substantially intact into the portal bloodstream with less gastrointestinal toxicity and better bioavailability than with the parent drug, and maintaining the efficacy of the parent drug at lower doses.

Gemcitabine hydrochloride (2',2'-difluoro-2'-deoxycytidine hydrochloride) is an anti-tumor agent, with known antiviral action, that is currently produced and marketed as Gemzar®; a lyophilised, powder formulation for treatment of various cancers. Gemzar®, a process for making it and methods for using it are described in U.S. Pat. No. 5,464,826 and U.S. Pat. No 4,808,614. Gemzar®is currently approved for the treatment of pancreatic cancer, breast cancer and non-small cell lung cancer (NSCLC) and is being evaluated for ovarian cancer. In addition Gemzar® may be used in the treatment of HCV as well as a modulator of immune function (see U.S. Pat. No 6,555,518). Gemzar® is currently administered by intravenous infusion at a dose of approximately 1000 to 1250 mg/m² over 30 minutes, once weekly for up to 7 weeks followed by a week of rest from treatment.

The use of gemcitabine orally may be limited by its poor oral bioavailability which is the result of first pass metabolism. Shipley L A. Et. al., "Metabolism and disposition of gemcitabine, and oncolytic deoxycytidine analog, in mice, rats, and dogs". *Drug Metabolism & Disposition.* 20(6):849-55, 1992. In addition, when dosed orally, gemcitabine is implicated in causing adverse dose-limiting intestinal lesions characterized by moderate-to-marked loss of mucosal epithelium (atrophic enteropathy) throughout the entire length of the intestinal tract in mice given a single oral (gavage) gemcitabine dose of 167, 333, or 500 mg/kg. Horton N D et.al., "Toxicity of single-dose oral gemcitabine in mice", American Association for Cancer Research, Poster Presentation, Orlando, Fla., Mar. 27-31, 2004. Comparable exposures via intravenous dosing in previous mouse studies did not result in death or gastrointestinal toxicity.

Methods for making prodrug and sustained released formulations of gemcitabine are well known in the art. Examples of such prodrugs and sustained released formulations can be found in WO 04/0412303 "Gemcitabine Prodrugs, Pharmaceutical Compositions and Uses Thereof", Gallop et. al.; WO 98/32762 "Gemcitabine Derivatives," Myhren, Finn, et al.; WO 02/09768 "Therapeutic polyesters and polyamides," Uhrich, Kathryn E.; WO 02/76476 "Prodrugs of anticancer agents based on substituted aromatic acids," Greenwald, Richard B., et al.; WO 02/65988, "Terminally-branched polymeric linkers and polymeric conjugates as prodrug," Choe, Yun Hwang, et al.

Gemcitabine amide derivatives have been described in the art as useful intermediates in the synthesis of gemcitabine, see e.g. Britton, et al., U.S. Pat. No. 5,420,266 and Grindey, et al., U.S. Pat. No. 5,464,826. and also useful as prodrug moieties for the administration of gemcitabine, see e.g. Gallop, et al., WO 04/041203.

There continues to be a need for a prodrug of gemcitabine that will allow for oral delivery, will pass through the intestinal tract intact without substantial degradation and deliver gemcitabine to the afflicted area with acceptable safety and efficacy.

Surprisingly, we have discovered a superior, novel amide derivative of gemcitabine, which traverses the enterocyte substantially intact; is hydrolyzed to gemcitabine without significant accumulation of deoxydifluorouridine (dFdU) the predominant gemcitabine metabolite in the liver, has less toxicity than oral gemcitabine, and maintains appropriate efficacy and safety profiles when administered orally.

BRIEF SUMMARY OF THE INVENTION

The present invention provides a compound of Formula I

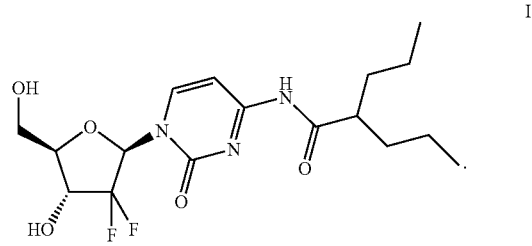

Another aspect of the invention provides for novel pharmaceutical compositions, comprising a compound of formula I and one or more pharmaceutically acceptable excipients.

The present invention also provides for the use of the compound of formula I for the treatment of susceptible neoplasms in a mammal in need of such treatment.

The present invention provides for the use of the compound of formula I for the treatment of susceptible viral infections in a mammal in need of such treatment.

The present invention also provides for the use of a compound of formula I for the manufacture of a medicament for the treatment of susceptible neoplasms or viral infections.

In addition, the present invention also provides a method for preparing the compound of formula I.

DETAILED DESCRIPTION OF THE INVENTION

As used herein the terms have the meanings indicated.

The term "mammal" is taken to mean any of various warm-blooded vertebrate animals of the class Mammalia, most preferably humans, characterized by a covering of hair on the skin and, in the female, milk-producing mammary glands for nourishing the young.

The term "pharmaceutically acceptable excipient" refers to a pharmaceutically acceptable formulation carrier, solution, or additive to enhance the formulation characteristics. Such excipients must be compatible with the other ingredients of the formulation and not deleterious to the recipient thereof and are well known to the skilled artisan, see e.g. Remingtons Pharmaceutical Sciences, 19$^{th}$ Edition, Mack Publishing Company, 1995.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Preferred co-crystals include p-toluenesulfonic acid and benzenesulfonic acid.

The term "pharmaceutically acceptable co-crystal" means one that is compatible with the other ingredients of the formulation and not deleterious to the recipient thereof.

The term "susceptible neoplasm" refers to an abnormal growth of tissue in mammals capable of being treated by the oral administration of the compound of formula I. As this prodrug will hydrolyze to gemcitabine, the administration of the prodrug is expected to have a broad spectrum of activity against a wide variety of tumor types, both solid and non-solid. Preferably, susceptible neoplasms include T-cell lymphoma, soft tissue sarcoma, pancreatic cancer, breast cancer, Hodgkin's lymphoma, non-Hodgkin's lymphoma, non-small cell lung cancer, ovarian cancer and bladder cancer.

The compounds of the invention are useful in the treatment of viral infections, particularly HCV.

The term "therapeutically effective amount" means the amount of compound/composition that will elicit the desired biologic or medicinal response of a tissue, system or mammal that is being sought by the researcher, physician or clinician.

Gemcitabine contains three derivatisable functional groups, the 3' and 5'hydroxyl groups and the N4-amino group. The compound of formula I can be prepared by using suitable protecting groups to block the 3' and 5' hydroxyl functions followed by acylation of the N4-amino group. Typical protecting groups are well know and appreciated in the art *Protecting Groups in Organic Synthesis*, $3^{rd}$ edition Theodora Greene, Peter Wuts (Wiley-Interscience) 1999. Acylation of the N4-amino group may be accomplished by reaction with an acid chloride or anhydride or by reaction with a carboxcylic acid in the presence of a coupling reagent, such as N,N-dicyclohexylcarbodiimide (DCC), N-ethyl-N'-(3-dimethylaminopropyl)-carbodiimide (EDC), 1,1-carbonyldiimidazole (CDI) or other similar reagents well known to one skilled in the art of organic chemistry. Alternatively, the compound of formula I may be prepared without the use of protecting groups. In this case, mixtures of mono-, di- and tri-adducts will be formed and the desired product may be separated from the mixture.

The following examples further illustrate the synthesis of compounds of the invention. All starting materials and reagents are well known and appreciated in the art and readily available or prepared by methods described herein. A process for preparing gemcitabine (2',2'-difluoro-2'-deoxycytidine), for example, is disclosed in U.S. Pat. No. 4,808,614.

EXAMPLE 1

1-(2,2-difluoro-2-deoxy-β-D-ribofuranosyl)-4-(2-propyl-1-oxopentyl)aminopyrimidin-2-one

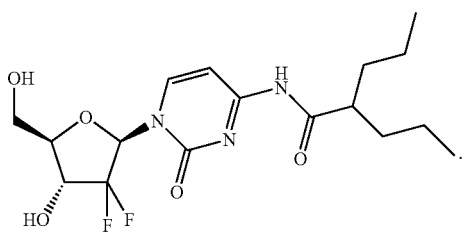

Dissolve 2',2'-difluoro-2'-deoxycytidine (10.0 g, 38.0 mmol) in anhydrous pyridine (100 mL) and cool to 0° C. while stirring under nitrogen. Add chlorotrimethylsilane (24.0 mL, 190.0 mmol) dropwise, maintaining an internal temperature <5° C. Continue stirring at 0° C. for 2 hours. In a separate flask, dissolve 2-propylpentanoic acid (6.0 g, 41.8 mmol) in anhydrous acetonitrile (100 mL). Add 1,1-carbonyldiimidazole (6.8 g, 41.8 mmol) in small portions over 30 minutes and stir for 2 hours. Add this acetonitrile solution dropwise to the pyridine solution at 0° C. and allow the reaction to come to ambient temperature. Heat the reaction at 45° C. overnight then cool to 30-35° C. and add 100 mL absolute ethanol and heat at 45° C. for 30 minutes. Add 50 mL water and heat at 45° C. for 5 hours then cool to ambient temperature and concentrate in vacuo. Partition the crude residue between ethyl acetate and water. Acidify to pH ~2 with phosphoric acid and separate the organic layer. Back extract the aqueous layer with additional ethyl acetate. Combine the organic solutions and wash with saturated sodium bicarbonate solution and saturated sodium chloride solution, dry over magnesium sulfate and concentrate in vacuo. Purify by silica gel chromatography (120 g) eluting with a gradient of 30% to 60% ethyl acetate in methylene chloride. Isolate desired product as a white crushable foam (11.2 g, 77% yield).

MS (ES): m/z 390.3=$[M+H]^+$ MS (ES): m/z 388.3=$[M-H]^{+1}$HNMR (400 MHz, DMSO-$d_6$) δ 0.83 (t, 6H), 1.15-1.36 (m, 6H), 1.46-1.55 (m, 2H), 2.60 (dddd, 1H, J=14.4, 9.6, 5.6, 5.6 Hz), (ddd, 1H, J=12.6, 6.2, 3.6 Hz), 3,77-3.81 (m, 1H), 3,87 (dt, 1H, J=8.4, 3.0 Hz), 4.12-4.22 (m, 1H), 5.27 (t, 1H, J=5.6 Hz), 6.15 (t, 1H, J=7.4 Hz), 6.29 (d, 1H, J=6.4 Hz), 7.31 (d, 1H, J=7.2 Hz), 8.23 (d, 1H, J=8.0 Hz), 11.03 (s, 1H).

EXAMPLE 2

1-(2,2-difluoro-2-deoxy-β-D-ribofuranosyl)-4-(2-propyl-1-oxopentyl)aminopyrimidin-2-one p-toluenesulfonic Acid hydrate Co-Crystal (2:1:1)

Dissolve 0.709 g (1.82 mmol) of the compound of Example 1 in 9 mL methanol. In a separate flask, prepare a 0.25 M aqueous stock solution of p-toluenesulfonic acid. Add 3.6 mL (0.9 mmol) of the aqueous solution dropwise. Add ~5 mL water and allow the mixture to stir at room temperature (~30 min) until precipitation occurs. Collect precipitated solid by vacuum filtration and allow to air dry.

Analytical Analysis of Co-Crystal:

Prepare solutions of known concentration of p-toluenesulfonic acid, gemcitabine and the compound of Example 1. Analyze a sample of the p-toluenesulfonic acid co-crystal of Example 1 to determine component composition.

For a 2:1:1 ratio of N-(2-propyl-pentanoyl)]-2',2'-difluoro-2'-deoxy-cytidine/p-toluenesulfonic acid/water, % toluenesulfonic acid determined:

Theory 17.8% p-toluenesulfonic acid

Found 19.1% p-toluenesulfonic acid

HPLC:

Column: Waters Atlantis dC18, 3.0 μm, 4.6 i.d.×150 mm

Column temp. 50° C.

UV wavelength: 248 nm

1. Mobile Phase

A. 5/95 acetonitrile/water+0.1% TFA

B. 50/50 acetonitrile/water+0.1% TFA

2. Gradient

| Time (min) | Solvent | |
|---|---|---|
| | % A | % B |
| 0 | 100 | 0 |
| 5 | 0 | 100 |
| 8 | 0 | 100 |
| 8.01 | 100 | 0 |
| 11 | end of run | |

EXAMPLE 3

1-(2,2-difluoro-2-deoxy-β-D-ribofuranosyl)-4-(2-propyl-1-oxopentyl)aminopyrimidin-2-one benzensulfonic Acid Co-Crystal (1:1)

To 5 mL of ethyl acetate, 550 mg of the compound of Example 1 is added. The mixture is heated to approximately 55° C. A one molar equivalence of benzensulfonic acid delivered as a stock solution is added. Additional ~10 mL of ethyl acetate is added with sonication, as needed, to break up the precipitate. The suspension is allowed to cool to room temperature and isolated by vacuum filtration. The isolated solid is allowed to air dry. MP: 171° C.

The compound of Formula I and solvates thereof are orally available and are normally administered orally, and so oral administration is preferred.

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like. The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations preferably contain at least 1% of the compound of the present invention, the active ingredient, but may be varied depending upon the particular form and may conveniently be between 1% to about 90% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, steric acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or fatty oil. Other dosage unit forms may contain other various materials that modify the physical form of the dosage unit, for example, as coatings. Preferably the dosage form is enteric coated. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of Formula I are generally effective over a wide dosage range. For example, dosages per day, in single or divided doses, normally fall within the range of about about 15 mg/day to about 200 mg/day, more preferably about 85 mg/day. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

pH Chemical Stability Assay

The pH chemical stability is assessed using a semi-automated HPLC technique. Samples of compound of formula I are prepared at 100 mcg/mL in five buffers representing the pH range throughout the gastrointestinal tract (pH1-pH8). Samples are loaded onto an HPLC autosampler incubated at 40° C. Samples are repeatedly injected on the HPLC at hourly intervals for up to 24 hours with an HPLC column that separates a compound of formula I from gemcitabine. The peak area of the compound of formula I is monitored by UV detection over time and are compared to initial peak areas to determine stability.

Less than 25% of the compound of Example 1 degraded to gemcitabine at pH range 1 to 8 after four hours.

Pharmacokinetic Assays

Mouse Pharmacokinetics

The pharmacokinetic profiles of gemcitabine and a compound of formula I, are assessed in male CD-1 mice following oral administration at doses selected to contain approximately 10 mg/kg of gemcitabine. Designated animals (n=3/time point/compound) are sacrificed at 0.08, 0.25, 0.5, 1, 2, and 6 hours after dosing, and systemic blood samples are collected into EDTA-treated tubes containing tetrahydrouridine (0.5 mM final concentration in blood) to inhibit further metabolism of gemcitabine. An additional 3 animals are sacrificed at 0.08 hours for collection of hepatic portal blood. Plasma is isolated by centrifugation and frozen prior to analysis. Plasma concentrations of gemcitabine and prodrugs are determined by LC/MS/MS analysis. Pharmacokinetic parameters are calculated using WinNonlin software (Pharsight Corp., Mountain View, Calif.). Pharmacokinetic parameters of each prodrug are compared to those determined from administration of oral gemcitabine hydrochloride in a similar study design.

The compound of Example 1 was extensively hydrolyzed in vivo to release gemcitabine when administered orally to CD-1 mice. The plasma exposure to gemcitabine was increased in CD-1 mice when the compound of Example 1 was administered, compared to direct oral administration of gemcitabine hydrochloride. The absorption of the intact prodrug is verified by relatively high concentrations of the compound of Example 1 in the hepatic portal plasma at 0.08 hours after oral dosing.

Monkey Pharmacokinetics Assay

The pharmacokinetic profiles of gemcitabine and a compound of formula I, are assessed in cynomolgus monkeys following oral and intravenous administration in a crossover design. Compounds are administered at doses selected to contain approximately 10 mg/kg of gemcitabine. Blood samples are collected into EDTA-treated tubes containing tetrahydrouridine (0.5 mM final concentration in blood) at designated intervals for up to 48 hours. Animals are pretreated with ranitidine (intravenous, 5 mg/kg) in the oral dosing periods. Plasma is isolated by centrifugation and frozen prior to analysis. Plasma concentrations of gemcitabine and a compound of formula I are determined by LC/MS/MS analysis. Pharmacokinetic parameters are determined using WinNonlin software (Pharsight Corp., Mountain View, Calif.).

The compound of Example 1 was extensively hydrolyzed in vivo to release gemcitabine when administered intravenously to cynomolgus monkeys. The oral exposure to gemcitabine was increased in cynomolgus monkeys approximately 5-fold when a compound of Example 1 was administered, compared to direct oral administration of gemcitabine hydrochloride.

Hydrolysis Assays

Small Intestine Homogenate Assay

To determine the stability of a compound of formula I to enzymatic hydrolysis in the intestine, crude homogenates of small intestinal epithelial cells are prepared from sections of the upper small intestine from CD-1 mice, beagle dogs, cynomolgus monkeys, and humans. Mouse and dog homogenates are prepared from freshly collected tissue, while monkey and human homogenates are prepared from previously frozen tissues. Cells are gently scraped from intestinal segments, pooled, and homogenized in 50 mM acetate buffer using Polytron (PT-10-85). Protein concentrations are determined by standard spectrophotometric techniques. The prepared homogenates are store at –70° C. before using.

The hydrolytic rates of a compound of formula I in small intestinal homogenates (SIH) is determined by incubating a compound of formula I (100 uM) with SIH (2.5-5 mg/mL of total protein) in acetate at pH 7.5 for up to 6 hours. Concentrations of gemcitabine released via hydrolysis is determined by LC/MS analysis after the reaction is quenched with acetonitrile. Hydrolysis rates are calculated at 30 minutes in screening experiments and from the slope of the linear portion of the hydrolysis vs. time curves in characterization studies of a compound of formula I.

The compound of Example 1 exhibited a slow rate of hydrolysis in the small intestine homogenate assay. The hydrolysis was slowest in monkey and human homogenates, with less than 3% of the total compound converted to gemcitabine in a 6 hour incubation.

Liver S9 Hydrolysis Assay

Hydrolysis of a compound of formula I by liver enzymes is determined by liver hydrolysis assay. Liver homogenates are prepared from CD-1 mouse, beagle dog, cynomolgus monkey, and human livers. Liver tissues are cut into small pieces using scissors, then, homogenized in 50 mM acetate buffer using Polytron (PT-10-85) for 1 min. Post-mitochondrial (S9) fractions are prepared from each by ultracentrifugation at 9,000×g at 4° C. for 10 min. Mouse, dog and monkey liver S9 fractions are prepared from freshly collected tissues, while human liver S9 are prepared from previously frozen tissue. After centrifugation, the supernatant is collected and protein concentrations are determined by standard spectrophotometric techniques. The prepared S9 fractions are store at –70° C. before using.

The hydrolytic rates of a compound of formula I in liver S9 is determined by incubating compound (10 uM) with S9 (2 mg/mL of total protein) in phosphate buffered saline at pH 8.0 for up to 6 hours. Concentrations of gemcitabine released via hydrolysis are determined by LC/MS analysis after the reaction is quenched with acetonitrile. Hydrolysis rates are calculated at 30 minutes in screening experiments and from the slope of the linear portion of the hydrolysis vs. time curves in characterization studies of a compound of formula I.

The compound of Example 1 was hydrolyzed in liver S9 of all species described. The hydrolysis was most rapid in monkey and human homogenates, with approximately 3.5% of the total compound converted to gemcitabine in a 6 hour incubation.

Toxicology Assays

4-Day Mouse Screen

To evaluate the toxicity produced by orally administered compound of formula I when administered daily to female CD-a mice for 4 days, the gastrointestinal toxicity profiles of a compound of formula I is compared with the historical results for gastrointestinal toxicity when gemcitabine is administered orally at 8 mg/kg in a 4-day mouse study.

Female CD-1 mice 5-8 weeks of age are dosed with a compound of formula I by oral gavage. A dose level is chosen to approximate a molar equivalent of 8-mg/kg gemcitabine. A dose volume of 10 mL/kg is used and doses are administered once daily on 4 consecutive days. Necropsy is performed approximately 5-8 hours following the $4^{th}$ dose.

Clinical signs, clinical chemistry, gross pathology, and limited histopathology (ileum, jejunum, and liver) are evaluated. There was a significant reduction in the severity of atrophic intestinal changes or enteropathy observed after dosing mice with an equivalent dose of the compound of Example 1 versus gemcitabine HCl.

14 Day Mouse Study

A 14-Day Mouse Study is conducted to evaluate whether a compound of formula I produces adverse effects in mice following 14 days of oral gavage dosing and to determine the plasma concentrations of a compound of formula I and its metabolites gemcitabine HCl and deoxydifluorouridine after 1 or 14 doses.

Male and female CD-1 mice 9-12 weeks of age are dosed with a compound of formula I rug by oral gavage. A range of doses is selected in an effort to determine a maximum tolerated dose and dose limiting toxicity. A dose volume of 10 mL/kg is used and doses are administered once daily.

Clinical signs, body weight, food consumption, hematology, clinical chemistry, plasma concentrations of a compound of formula I and metabolites gemcitabine HCl and deoxydifluorouridine, and pathology (including gross pathology, organ weights, and histopathology) are evaluated.

On a molar equivalent basis, the compound of Example 1 is associated with less enteropathy than gemcitabine HCl while resulting in approximately twice the systemic. exposure to gemcitabine HCL.

7-Day Dog Study

To evaluate the toxicity profile of a compound of formula I when administered to Beagle dogs for 7 days, and to determine the plasma concentrations of a compound of formula I and metabolites gemcitabine HCl and deoxydifluorouridine after 1 or 7 doses, a 7-day dog study is conducted.

Male and female beagle dogs 6-48 months of age are dosed orally via capsule with a compound of formula I. A range of doses is selected in an effort to determine a maximum tolerated dose and dose limiting toxicity. A dose volume of 1 mL/kg is used and doses aree administered once daily.

Clinical signs, body weight, food consumption, body temperature, hematology (including coagulation), clinical chemistry, urinalysis, plasma concentrations of the compound of Example I and its metabolites gemcitabine HCl and deoxydifluorouridine, and pathology (including gross pathology, organ weights, and histopathology) were evaluated. Hematotoxicity and the other toxicities, including GI toxicity, are consistent with what has been previously described for parenteral gemcitabine. Therefore, none of these toxicities were unique to the oral dosing route.

In Vivo Assay

HCT-116 colon tumor cells are grown in vitro under standard tissue culture conditions, harvested, washed, and $5 \times 10^6$ cells (1:1 suspension in Matrigel, Collaborative Biomedical Products, Inc) are injected subcutaneously in the rear flank of female nude mice (Charles River, CD1 nu/nu, 24-27 g, irradiated with 450 Rads within 24 h of implantation). Tumors are allowed to grow to ~100 mm$^3$ before initiation of therapy. Vehicle control, a compound of formula I or gemcitabine-HCl at various dose levels are administered to the mice by oral gavage (10 ml/kg volume) at the times indicated in the individual experiments. Compounds are administered either daily for fourteen days, every other day for a total of seven doses, or every third day for a total of four doses. For the every day dosing schedule, a compound of formula I is formulated in 100 mM sodium phosphate buffer, pH 6.0, and is formulated in 1% sodium carboxymethylcellulose, 0.5% sodium lauryl sulfate, 0.05% Antifoam 150 and 0.085% povidone for the every other day and every third day dosing schedules. Gemcitabine-HCl is prepared in physiological saline for oral administration. Tumor size is determined by caliper measurements and tumor volume (mm$^3$) is estimated from the formula l×w$^2$×0.536, where l is the larger and w is the smaller of perpendicular diameters. All data (tumor measurements and animal weights) are captured twice-weekly beginning with the start of therapy and analyzed using a computer based tumor measurement system.

The antitumor efficacy observed with the compound of Example 1 was comparable to that obtained with an equivalent dose of gemcitabine-HCl. However, treatment with the compound of Example 1 resulted in less overall toxicity compared to animals that received an equivalent amount of gemcitabine-HCl.

We claim:

1. A compound of the formula

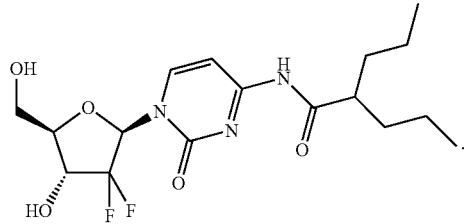

2. A compound which is 1-(2,2-difluoro-2-deoxy-b-D-ribofuranosyl)-4-(2-propyl-1-oxopentyl)aminopyrimidin-2-one p-toluenesulfonic acid co-crystal.

3. The compound of claim 2 which is 1-(2,2-difluoro-2-deoxy-b-D-ribofuranosyl)-4-(2-propyl-1-oxopentyl)aminopyrimidin-2-one p-toluenesulfonic acid hydrate co-crystal (2:1:1).

4. A pharmaceutical composition comprising a compound of claim 3 and a pharmaceutically acceptable excipient.

5. The pharmaceutical composition of claim 4, wherein the composition is enteric coated.

6. A compound which is 1-(2,2-difluoro-2-deoxy-β-D-ribofuranosyl)-4-(2-propyl-1-oxopentyl)aminopyrimidin-2-one benzenesulfonic acid co-crystal (1:1).

* * * * *

UNITED STATES PATENT AND TRADEMARK OFFICE
CERTIFICATE OF CORRECTION

PATENT NO. : 7,691,827 B2  Page 1 of 1
APPLICATION NO. : 11/719705
DATED : April 6, 2010
INVENTOR(S) : David Michael Bender et al.

It is certified that error appears in the above-identified patent and that said Letters Patent is hereby corrected as shown below:

1) Title page, column 2, line 9:
Delete "Greenwald" and
Insert --Greenwald, et al.--, therefor.

2) Claim 2, column 10, line 27 (approx.):
Delete "deoxy-b-D" and
Insert --deoxy-β-D--, therefor.

3) Claim 3, column 10, line 31:
Delete "deoxy-b" and
Insert --deoxy-β--, therefor.

Signed and Sealed this

Thirteenth Day of July, 2010

David J. Kappos
*Director of the United States Patent and Trademark Office*